United States Patent
Addison et al.

(10) Patent No.: US 8,932,219 B2
(45) Date of Patent: Jan. 13, 2015

(54) SYSTEMS AND METHODS FOR MONITORING HEART RATE AND BLOOD PRESSURE CORRELATION

(75) Inventors: Paul Stanley Addison, Edinburgh (GB); James Watson, Dunfermline (GB); Rakesh Sethi, Vancouver (CA)

(73) Assignee: Nellcor Puritan Bennett Ireland, Galway (IE)

( * ) Notice: Subject to any disclaimer, the term of this patent is extended or adjusted under 35 U.S.C. 154(b) by 209 days.

(21) Appl. No.: 13/528,755

(22) Filed: Jun. 20, 2012

(65) Prior Publication Data

US 2012/0259235 A1    Oct. 11, 2012

Related U.S. Application Data

(63) Continuation of application No. 12/398,826, filed on Mar. 5, 2009, now Pat. No. 8,216,136.

(51) Int. Cl.

| | |
|---|---|
| *A61B 5/02* | (2006.01) |
| *G06F 19/00* | (2011.01) |
| *A61B 5/0205* | (2006.01) |
| *A61B 5/021* | (2006.01) |
| *A61B 5/00* | (2006.01) |

(52) U.S. Cl.
CPC .......... *G06F 19/345* (2013.01); *A61B 5/0205* (2013.01); *A61B 5/021* (2013.01); *G06F 19/3406* (2013.01); *A61B 5/7264* (2013.01)
USPC ........................................ 600/301

(58) Field of Classification Search
None
See application file for complete search history.

(56) References Cited

U.S. PATENT DOCUMENTS

| | | |
|---|---|---|
| 3,654,445 A | 4/1972 | Mikkelsen et al. |
| 3,835,840 A | 9/1974 | Mount |
| 4,228,506 A | 10/1980 | Ripley et al. |
| 4,561,447 A | 12/1985 | Kawamura et al. |
| 4,676,253 A | 6/1987 | Newman |
| 4,685,464 A | 8/1987 | Goldberger et al. |
| 4,714,080 A | 12/1987 | Edgar, Jr. et al. |
| 4,729,382 A | 3/1988 | Schaffer |
| 4,768,516 A | 9/1988 | Stoddart et al. |
| 4,796,636 A | 1/1989 | Branstetter et al. |
| 4,802,222 A | 1/1989 | Weaver |

(Continued)

FOREIGN PATENT DOCUMENTS

| | | |
|---|---|---|
| EP | 0352923 | 1/1990 |
| EP | 0443267 | 8/1991 |

(Continued)

OTHER PUBLICATIONS

International Search Report PCT/GB2010/000378, 6 pages, mailed Jul. 7, 2010.

(Continued)

*Primary Examiner* — Brian T Gedeon
(74) *Attorney, Agent, or Firm* — Shvarts & Leiz LLP

(57) ABSTRACT

Systems and methods are provided for monitoring a correlation between heart rate and blood pressure in a patient. When a characteristic of the correlation exceeds a threshold, a patient status indicator signal is sent to a monitoring device. In some embodiments, the patient status indicator signal indicates a particular medical condition or alerts a care provider to a change in status. In some embodiments, the heart rate signal is used to improve a blood pressure estimate generated by a different signal. In some embodiments, the heart rate, blood pressure and correlation signals are used in a predictive mathematical model to estimate patient status or outcome.

19 Claims, 7 Drawing Sheets

(56) References Cited

U.S. PATENT DOCUMENTS

| | | |
|---|---|---|
| 4,802,486 A | 2/1989 | Goodman et al. |
| 4,817,623 A | 4/1989 | Stoddart et al. |
| 4,830,017 A | 5/1989 | Perry et al. |
| 4,836,213 A | 6/1989 | Wenzel et al. |
| 4,854,327 A | 8/1989 | Kunig |
| 4,854,699 A | 8/1989 | Edgar, Jr. |
| 4,898,176 A | 2/1990 | Petre |
| 4,911,167 A | 3/1990 | Corenman et al. |
| 4,924,871 A | 5/1990 | Honeyager |
| 4,928,692 A | 5/1990 | Goodman et al. |
| 4,928,700 A | 5/1990 | Harada |
| 4,934,372 A | 6/1990 | Corenman et al. |
| 4,951,679 A | 8/1990 | Harada |
| 4,976,268 A | 12/1990 | Kurosawa et al. |
| 4,987,900 A | 1/1991 | Eckerle |
| 5,007,423 A | 4/1991 | Branstetter et al. |
| 5,020,540 A | 6/1991 | Chamoun |
| 5,065,765 A | 11/1991 | Eckerle |
| 5,077,667 A | 12/1991 | Brown et al. |
| 5,094,239 A | 3/1992 | Jaeb et al. |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,143,078 A | 9/1992 | Mather et al. |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,187,672 A | 2/1993 | Chance et al. |
| 5,188,108 A | 2/1993 | Secker |
| 5,204,922 A | 4/1993 | Weir |
| 5,216,598 A | 6/1993 | Branstetter et al. |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,285,783 A | 2/1994 | Secker |
| 5,285,784 A | 2/1994 | Seeker |
| 5,289,823 A | 3/1994 | Eckerle |
| 5,309,917 A | 5/1994 | Wang et al. |
| 5,353,799 A | 10/1994 | Chance |
| 5,431,159 A | 7/1995 | Baker et al. |
| 5,450,852 A | 9/1995 | Archibald et al. |
| 5,467,771 A | 11/1995 | Narimatsu et al. |
| RE35,122 E | 12/1995 | Corenman et al. |
| 5,482,036 A | 1/1996 | Diab et al. |
| 5,490,505 A | 2/1996 | Diab et al. |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari et al. |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan et al. |
| 5,590,650 A | 1/1997 | Genova |
| 5,595,176 A | 1/1997 | Yamaura |
| 5,617,868 A | 4/1997 | Harada et al. |
| 5,632,272 A | 5/1997 | Diab et al. |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa et al. |
| 5,682,898 A | 11/1997 | Aung et al. |
| 5,685,299 A | 11/1997 | Diab et al. |
| 5,685,316 A | 11/1997 | Schookin et al. |
| 5,692,503 A | 12/1997 | Kuenstner |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,738,104 A | 4/1998 | Lo et al. |
| 5,743,856 A | 4/1998 | Oka et al. |
| 5,755,669 A | 5/1998 | Ono et al. |
| 5,762,610 A | 6/1998 | Narimatsu et al. |
| 5,769,785 A | 6/1998 | Diab et al. |
| 5,772,601 A | 6/1998 | Oka et al. |
| 5,772,602 A | 6/1998 | Sakai et al. |
| 5,776,071 A | 7/1998 | Inukai et al. |
| 5,778,881 A | 7/1998 | Sun et al. |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias et al. |
| 5,827,182 A | 10/1998 | Raley et al. |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,857,975 A | 1/1999 | Golub |
| 5,873,834 A | 2/1999 | Yanagi et al. |
| 5,879,294 A | 3/1999 | Anderson et al. |
| 5,891,025 A | 4/1999 | Buschmann et al. |
| 5,904,654 A | 5/1999 | Wohltmann et al. |
| 5,924,980 A | 7/1999 | Coetzee |
| 5,934,277 A | 8/1999 | Mortz |
| 5,941,828 A | 8/1999 | Archibald et al. |
| 5,964,711 A | 10/1999 | Voss et al. |
| 5,978,693 A | 11/1999 | Hamilton et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,018,673 A | 1/2000 | Chin et al. |
| 6,022,320 A | 2/2000 | Ogura et al. |
| 6,027,452 A | 2/2000 | Flaherty et al. |
| 6,027,453 A | 2/2000 | Miwa et al. |
| 6,027,455 A | 2/2000 | Inukai et al. |
| 6,035,223 A | 3/2000 | Baker, Jr. |
| 6,036,642 A | 3/2000 | Diab et al. |
| 6,045,509 A | 4/2000 | Caro et al. |
| 6,050,951 A | 4/2000 | Friedman et al. |
| 6,067,462 A | 5/2000 | Diab et al. |
| 6,070,098 A | 5/2000 | Moore-Ede et al. |
| 6,083,171 A | 7/2000 | Ono et al. |
| 6,095,987 A | 8/2000 | Shmulewitz |
| 6,117,075 A | 9/2000 | Barnea |
| 6,135,952 A | 10/2000 | Coetzee |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,206,830 B1 | 3/2001 | Diab et al. |
| 6,208,951 B1 | 3/2001 | Kumar et al. |
| 6,216,021 B1 | 4/2001 | Franceschini et al. |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,363,270 B1 | 3/2002 | Colla et al. |
| 6,371,921 B1 | 4/2002 | Caro et al. |
| 6,374,129 B1 | 4/2002 | Chin et al. |
| 6,385,471 B1 | 5/2002 | Mortz |
| 6,405,069 B1 | 6/2002 | Oraevsky et al. |
| 6,430,513 B1 | 8/2002 | Wang et al. |

(56) References Cited

U.S. PATENT DOCUMENTS

| | | |
|---|---|---|
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,501,975 B2 | 12/2002 | Diab et al. |
| 6,506,161 B2 | 1/2003 | Brockway et al. |
| 6,510,329 B2 | 1/2003 | Heckel |
| 6,511,438 B2 | 1/2003 | Bernstein et al. |
| 6,514,211 B1 | 2/2003 | Baura |
| 6,524,240 B1 | 2/2003 | Thede |
| 6,561,986 B2 | 5/2003 | Baura et al. |
| 6,571,193 B1 | 5/2003 | Unuma et al. |
| 6,587,703 B2 | 7/2003 | Cheng et al. |
| 6,589,185 B1 | 7/2003 | Archibald et al. |
| 6,594,511 B2 | 7/2003 | Stone et al. |
| 6,597,931 B1 | 7/2003 | Cheng et al. |
| 6,599,251 B2 | 7/2003 | Chen et al. |
| 6,602,199 B2 | 8/2003 | Chen et al. |
| 6,602,201 B1 | 8/2003 | Malecha et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,668,182 B2 | 12/2003 | Hubelbank |
| 6,684,090 B2 | 1/2004 | Ali et al. |
| RE38,476 E | 3/2004 | Diab et al. |
| 6,699,194 B1 | 3/2004 | Diab |
| 6,714,803 B1 | 3/2004 | Mortz |
| RE38,492 E | 4/2004 | Diab et al. |
| 6,719,689 B2 | 4/2004 | Munneke et al. |
| 6,767,328 B2 | 7/2004 | Kulik |
| 6,773,397 B2 | 8/2004 | Kelly |
| 6,783,498 B2 | 8/2004 | Sackner et al. |
| 6,816,741 B2 | 11/2004 | Diab |
| 6,822,564 B2 | 11/2004 | Al-Ali |
| 6,826,419 B2 | 11/2004 | Diab et al. |
| 6,827,688 B2 | 12/2004 | Goto et al. |
| 6,845,256 B2 | 1/2005 | Chin et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,869,403 B2 | 3/2005 | Narimatsu et al. |
| 6,929,610 B2 | 8/2005 | Forstner |
| 6,970,792 B1 | 11/2005 | Diab |
| 6,987,994 B1 | 1/2006 | Mortz |
| 6,990,426 B2 | 1/2006 | Yoon et al. |
| 6,996,427 B2 | 2/2006 | Ali et al. |
| 7,004,907 B2 | 2/2006 | Banet et al. |
| 7,016,715 B2 | 3/2006 | Stetson |
| 7,043,293 B1 | 5/2006 | Baura |
| 7,044,918 B2 | 5/2006 | Diab |
| 7,070,566 B2 | 7/2006 | Medero et al. |
| 7,072,704 B2 | 7/2006 | Bucholz |
| 7,074,192 B2 | 7/2006 | Friedman et al. |
| 7,079,035 B2 | 7/2006 | Bock et al. |
| 7,087,025 B2 | 8/2006 | Baruch |
| 7,130,672 B2 | 10/2006 | Pewzner et al. |
| 7,139,599 B2 | 11/2006 | Terry |
| 7,173,525 B2 | 2/2007 | Albert |
| 7,181,264 B2 | 2/2007 | Wiesmann et al. |
| 7,184,809 B1 | 2/2007 | Sterling et al. |
| 7,201,734 B2 | 4/2007 | Hickle |
| 7,215,984 B2 | 5/2007 | Diab et al. |
| 7,215,986 B2 | 5/2007 | Diab et al. |
| 7,231,240 B2 | 6/2007 | Eda et al. |
| 7,247,154 B2 | 7/2007 | Hickle |
| 7,252,636 B2 | 8/2007 | Brown |
| 7,254,433 B2 | 8/2007 | Diab et al. |
| 7,260,425 B2 | 8/2007 | Chin et al. |
| 7,301,630 B2 | 11/2007 | Furukawa |
| 7,320,030 B2 | 1/2008 | Brown |
| 7,335,162 B2 | 2/2008 | Eide |
| 7,367,339 B2 | 5/2008 | Hickle |
| 7,376,238 B1 | 5/2008 | Rivas et al. |
| 7,383,070 B2 | 6/2008 | Diab et al. |
| 7,390,300 B2 | 6/2008 | Inukai et al. |
| 7,390,301 B2 | 6/2008 | Skrabal et al. |
| 7,392,075 B2 | 6/2008 | Baker, Jr. |
| 7,393,327 B2 | 7/2008 | Inukai et al. |
| 7,400,257 B2 | 7/2008 | Rivas |
| 7,438,687 B2 | 10/2008 | Lewicke |
| 7,440,787 B2 | 10/2008 | Diab |
| 7,455,643 B1 | 11/2008 | Li et al. |
| 7,474,907 B2 | 1/2009 | Baker, Jr. |
| 7,481,772 B2 | 1/2009 | Banet |
| 7,485,095 B2 | 2/2009 | Shusterman |
| 7,623,909 B2 | 11/2009 | Sanghera et al. |
| 2002/0103423 A1 | 8/2002 | Chin et al. |
| 2003/0032871 A1 | 2/2003 | Selker |
| 2004/0064020 A1 | 4/2004 | Diab et al. |
| 2004/0068164 A1 | 4/2004 | Diab et al. |
| 2004/0204638 A1 | 10/2004 | Diab et al. |
| 2004/0236187 A1 | 11/2004 | Bock |
| 2004/0236196 A1 | 11/2004 | Diab et al. |
| 2005/0070773 A1 | 3/2005 | Chin et al. |
| 2005/0070775 A1 | 3/2005 | Chin et al. |
| 2005/0119708 A1 | 6/2005 | Haefner |
| 2005/0148885 A1 | 7/2005 | Tweed et al. |
| 2005/0209517 A1 | 9/2005 | Diab et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0155206 A1 | 7/2006 | Lynn |
| 2006/0173257 A1 | 8/2006 | Nagai et al. |
| 2006/0206021 A1 | 9/2006 | Diab |
| 2006/0209631 A1 | 9/2006 | Melese et al. |
| 2006/0217609 A1 | 9/2006 | Diab et al. |
| 2006/0217614 A1 | 9/2006 | Takala et al. |
| 2006/0217628 A1 | 9/2006 | Huiku |
| 2006/0224053 A1 | 10/2006 | Black et al. |
| 2006/0241975 A1 | 10/2006 | Brown |
| 2006/0285736 A1 | 12/2006 | Brown |
| 2006/0287603 A1 | 12/2006 | Bartnik et al. |
| 2007/0015976 A1 | 1/2007 | Miesel et al. |
| 2007/0060803 A1 | 3/2007 | Liljeryd et al. |
| 2007/0066910 A1 | 3/2007 | Inukai et al. |
| 2007/0083093 A1 | 4/2007 | Diab |
| 2007/0083097 A1 | 4/2007 | Fujiwara et al. |
| 2007/0118045 A1 | 5/2007 | Naghavi et al. |
| 2007/0129647 A1 | 6/2007 | Lynn |
| 2007/0149890 A1 | 6/2007 | Li et al. |
| 2007/0179350 A1 | 8/2007 | Nadeau |
| 2007/0191693 A1 | 8/2007 | Peng |
| 2007/0203417 A1 | 8/2007 | Wasserman et al. |
| 2007/0225581 A1 | 9/2007 | Diab et al. |
| 2007/0225582 A1 | 9/2007 | Diab et al. |
| 2007/0249467 A1 | 10/2007 | Hong et al. |
| 2007/0299328 A1 | 12/2007 | Chin et al. |
| 2008/0015451 A1 | 1/2008 | Hatib et al. |
| 2008/0021379 A1 | 1/2008 | Hickle |
| 2008/0030468 A1 | 2/2008 | Ali et al. |
| 2008/0033305 A1 | 2/2008 | Hatib et al. |
| 2008/0077023 A1 | 3/2008 | Campbell et al. |
| 2008/0081963 A1 | 4/2008 | Naghavi et al. |
| 2008/0082018 A1 | 4/2008 | Sackner et al. |
| 2008/0132798 A1 | 6/2008 | Hong et al. |
| 2008/0146901 A1 | 6/2008 | Katura et al. |
| 2008/0183058 A1 | 7/2008 | Mannheimer |
| 2008/0198361 A1 | 8/2008 | Kaushal et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2008/0255436 A1 | 10/2008 | Baker |
| 2008/0262362 A1 | 10/2008 | Kolluri et al. |
| 2009/0048497 A1 | 2/2009 | Keren |

FOREIGN PATENT DOCUMENTS

| | | |
|---|---|---|
| EP | 0755221 | 1/1997 |
| EP | 1785087 | 5/2007 |

(56) References Cited

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 3124073 | 1/1990 |
| JP | 03231630 | 10/1991 |
| JP | 5049624 | 3/1993 |
| JP | 06142082 | 5/1994 |
| JP | 07136136 | 5/1995 |
| JP | 11155841 | 6/1999 |
| JP | 03225268 | 12/2003 |
| WO | WO 2005/020120 | 3/2005 |
| WO | WO 2007/013326 | 2/2007 |
| WO | WO 2008/097411 | 8/2008 |

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. CH., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994, pp. 1-446.

Fung, YC, Biomechanics: Circulation, 2nd Edition, New York, Springer, 1997, pp. 1-571.

Geddes, LA, Handbook of Blood Pressure Measurement, Clifton, New Jersey, Humana Press, 1991, pp. 1-168.

Millasseau, Sandrine C, Guigui, Franck G, Kelly, Ronan P., Prasad, Krishna, Cockcroft, John R., Ritter, James M., Chowienczyk, Philip J., "Noninvasive Assessment of the Digital Volume Pulse: Comparison with the Peripheral Pressure Pulse, Hypertension," vol. 36, No. 6, Dec. 2000, pp. 952-956.

Moyle, John TB, Hahn, CEW, Adams, Anthony P, Pulse Oximetry, Revised Edition, London, BMJ, 1998, pp. 1-140.

Nara, Andrew R., Burns, Michael P., Downs, W. Gregory, Blood Pressure, Redmond, Washington, SpaceLabs, 1989, pp. 1-109.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990, pp. 1-456.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb. 1991, pp. 39-54.

Young, Christopher C., Mark, Jonathan B., White, William, Debree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Communication Pursuant to Article 94(3) EPC issued by the European Patent Office in connection with counterpart European Patent Application No. 10 709 252.0, dated Jun. 5, 2013, 4 pages.

SYSTEMS AND METHODS FOR MONITORING HEART RATE AND BLOOD PRESSURE CORRELATION

This application is a continuation of U.S. patent application Ser. No. 12/398,826 filed Mar. 5, 2009, now U.S. Pat. No. 8,216,136, the contents of which are incorporated herein by reference in its entirety.

SUMMARY

The present disclosure relates to simultaneous blood pressure and heart rate monitoring to determine patient status, and more particularly, relates to monitoring the correlation of blood pressure and heart rate to alert a care provider to a patient condition. Broadly, a correlation is a measurement of the degree to which heart rate and blood pressure tend to increase (and decrease) simultaneously.

A patient's status may be determined by analyzing a correlation between the heart rate (HR) and blood pressure (BP). A HR signal and a BP signal may be received and a correlation calculated. A characteristic of the correlation may be identified. In some embodiments, this characteristic includes a change in HR relative to a change in BP, or a rate of change in HR relative to a rate of change in BP. Once identified, this characteristic may be compared to a threshold. In some embodiments, comparing the characteristic to a threshold identifies whether the correlation is positive or negative.

A patient status indicator signal may be generated in response to the threshold comparison. In some embodiments, the characteristic and the threshold correspond to a particular patient condition and the patient status indicator signal includes an indication of the corresponding condition. In some embodiments, generating the patient status indicator signal includes querying a lookup table to retrieve a value for a patient status.

The patient status indicator signal may be transmitted to an output device and used as the basis for a patient status indication. In some embodiments, indicating a patient status includes at least one of displaying the correlation characteristic on a screen, displaying a message associated with the patient status indicator signal, displaying a color associated with the patient status indicator signal, displaying a graphic associated with the patient status indicator signal, and producing a sound associated with the patient status indicator signal.

In some embodiments, a current BP may be calculated based at least in part on the received HR signal. In some embodiments, at least one of a patient outcome and current status may be predicted using a computational model based at least in part on HR and BP signals.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Heart rate (HR) and blood pressure (BP) are generally related according to $$BP = HR \times SV \times TPR$$

where SV is the stroke volume and TPR is the total peripheral resistance. The stroke volume is the volume of blood leaving the heart in a given contraction, while TPR measures the resistance exerted by the remainder of the cardiovascular system on the heart.

This equation appears to suggest a positive correlation between changes in HR and changes in BP, i.e. an increase in HR might be accompanied by an increase in BP and vice versa. Similarly, a decrease in HR might be accompanied by an decrease in BP and vice versa.

Figure 1A:
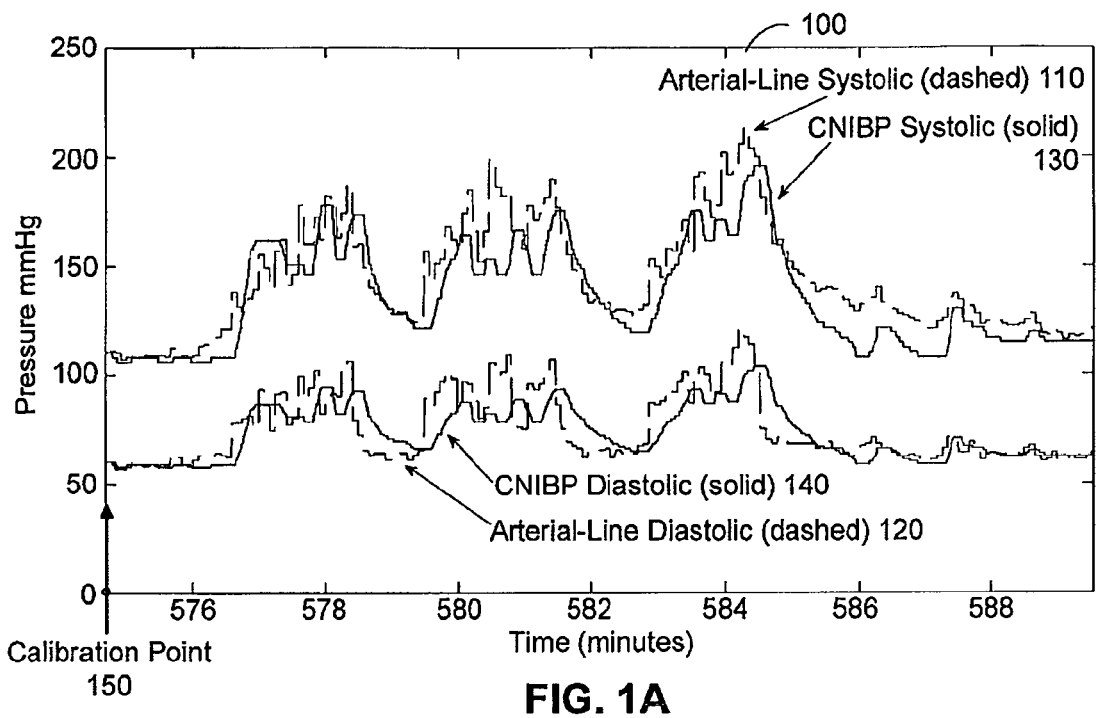
FIGS. 1A and 1B depict comparisons of an arterial line blood pressure (BP) measurement with a BP estimate based on heart rate (HR)

Under normal conditions, HR and BP signals often exhibit such a correlation. In these conditions, BP can be reasonably estimated by some increasing function of HR. For example, FIGS. 1A and 1B each depict a comparison of an arterial line BP measurement with a BP estimate based on an increasing function of HR. In FIG. 1A, this increasing function is a linear function, while in FIG. 1B, this increasing function is a non-linear function.

Specifically, graph 100 of FIG. 1A depicts a subject's systolic and diastolic BP during exercise as determined by two different BP measurement methods: an arterial line measurement and an HR-based estimate. Arterial line systolic BP measurement 110 and arterial line diastolic BP measurement 120 are shown as dashed lines, while HR-based systolic estimate 130 and HR-based diastolic estimate 140 are shown as solid lines. In FIG. 1A, the HR-based estimates 130 and 140 are determined in accordance with the linear equation $$BP = a + b \cdot (HR)$$

where b=2.26 for the systolic estimate 130 and b=1.15 for the diastolic estimate 140. The values for a were determined by calibration at a known BP and known HR at calibration point 150 and the values for b were chosen to best match the data. Values for b could also be estimated from the HR using a linear or non-linear relationship derived from historical data.

Figure 1B:
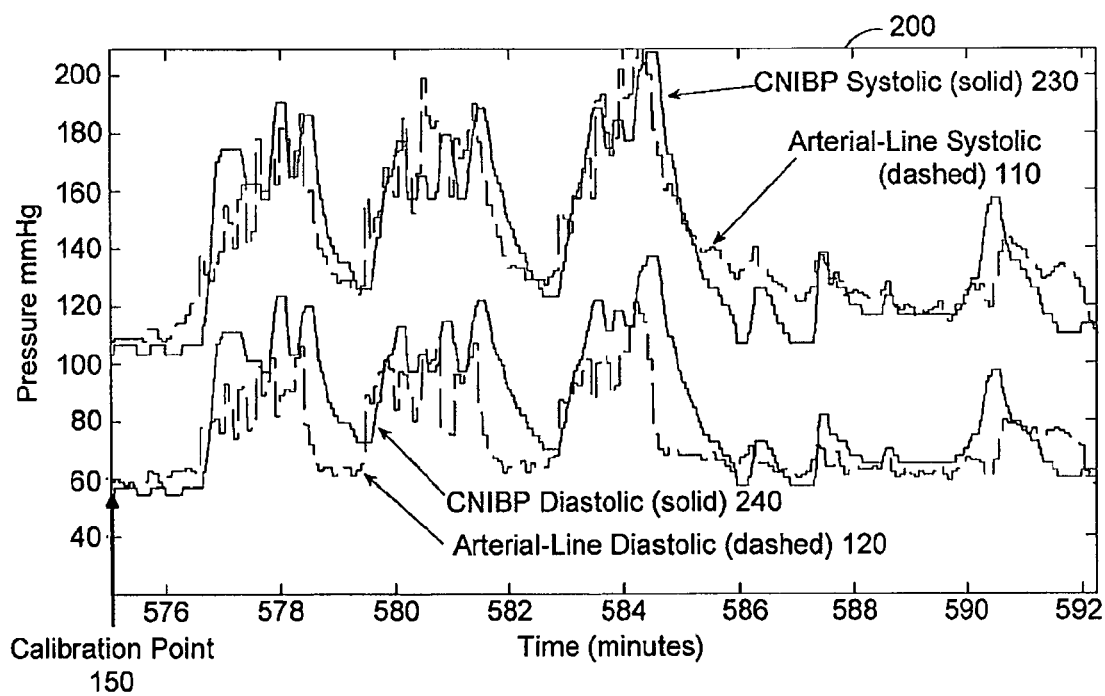
Figure 2:
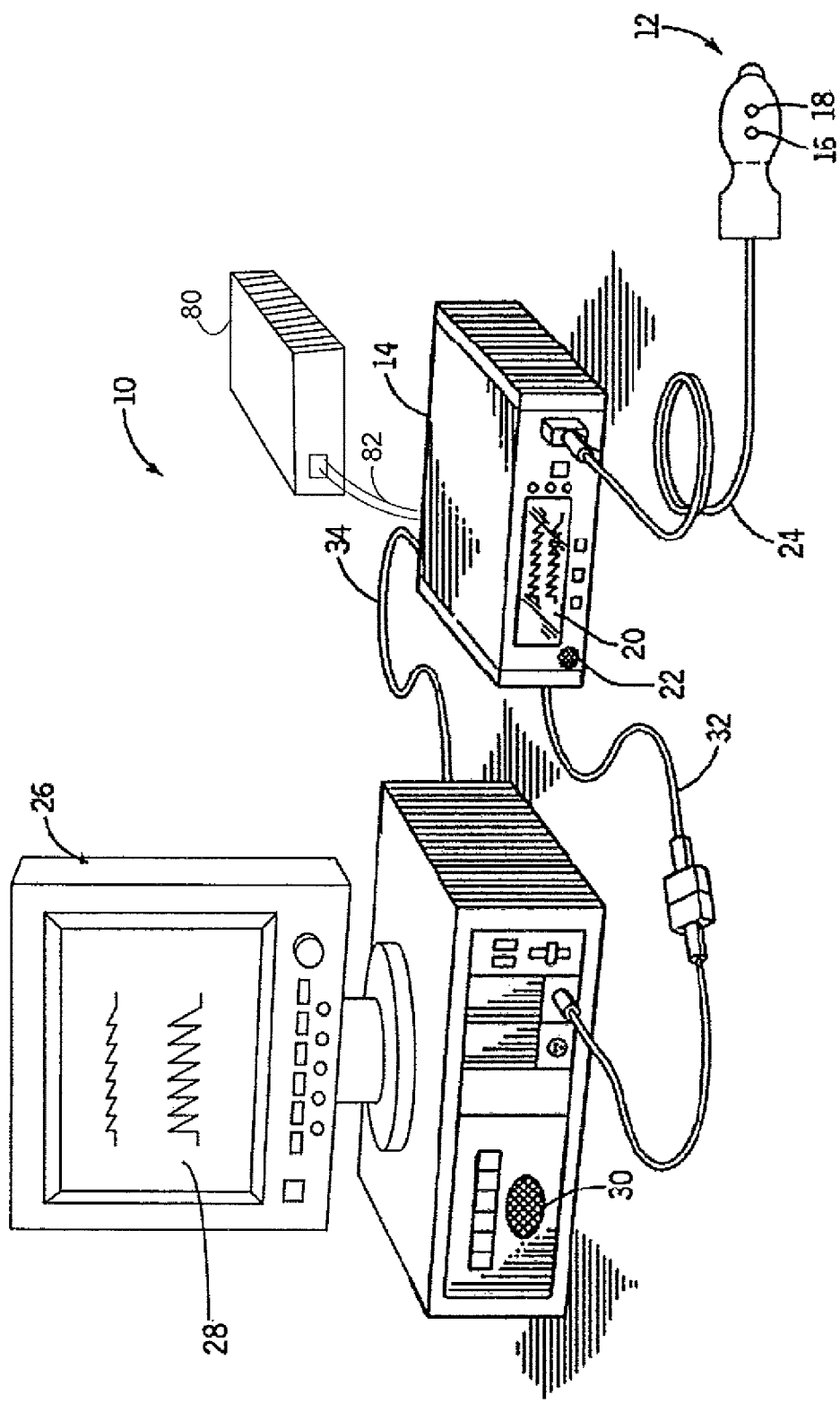
FIG. 2 shows an illustrative BP/HR monitoring system in accordance with an embodiment.

FIG. 1B depicts a comparison of an arterial line BP measurement with a BP estimate based non-linearly on HR. As in FIG. 1A, FIG. 1B shows a graph 200 of a subject's systolic BP 110 and diastolic BP 120 during exercise as determined by an arterial line measurement (as in FIG. 1A). Graph 200 also depicts a non-linear HR-based systolic estimate 230 and a non-linear HR-based diastolic estimate 240 as solid lines. In FIG. 2, the HR-based estimates 230-240 are determined in accordance with the non-linear equation $$BP = a + b \cdot \ln(HR)$$

where b=200 for the systolic estimate 230, b=150 for the diastolic estimate 240. The values for a and b were determined as discussed above with reference to FIG. 1A.

The linear and non-linear relationships used to provide estimates of BP from HR in FIGS. 1A and 1B are both increasing functions, and thus exhibit a positive correlation between HR and BP. However, the additional factors of SV and TPR have, in general, a complex, non-linear and non-monotonic dependence on both BP and HR. This non-monotonic dependence becomes clear when a patient suffers from a pathological condition or is in a distressed state.

Indeed, there are many medical conditions in which HR and BP are negatively correlated. For example, uncontrolled atrial fibrillation is a condition characterized by an abnormally rapid heart rate caused by unregulated firing of electrical pulses within the heart muscles. This rapid firing induces an elevated heart rate (known as tachycardia) while simultaneously preventing the ventricles from filling completely with blood before the next contraction. In this condition, HR increases while SV decreases. As a result, the total volume of blood pumped to the body from the heart (the product of SV and HR, also known as the cardiac output) can decrease during atrial fibrillation, leading to a decrease in BP.

Detecting a change in the correlation of BP and HR can alert medical providers to potentially dangerous patient conditions. This correlation is difficult or impossible for a care provider to monitor from intermittent BP and HR readings. A monitoring system that tracks this correlation automatically for a care provider and indicates a patient status in response to the correlation provides a new tool in patient diagnosis and treatment. In light of this observation, the present disclosure relates to systems and methods for simultaneous blood pressure and heart rate monitoring to determine patient status, and more particularly, relates to monitoring the correlation of blood pressure and heart rate to alert a care provider to a patient condition.

FIG. 2 shows an illustrative BP/HR monitoring system 10. System 10 may include a sensor unit 12 and a monitor 14. In an embodiment, sensor unit 12 includes sensors 16 and 18 capable of detecting a signal carrying information about a patient's HR and BP, respectively. Sensor 16 may detect any signal that carries information about a patient's HR, such as an electrocardiograph signal or the pulsatile force exerted on the walls of an artery using, for example, a piezoelectric transducer. Sensor 18 may detect any signal carrying information about a patient's BP and may employ, for example, oscillometric methods using piezoelectric transducers or invasive arterial line methods. According to another embodiment, system 10 may include a plurality of sensors forming a sensor array in lieu of either or both of sensors 16 and 18. Although only two sensors 16 and 18 are illustrated in the sensor unit 12 of FIG. 3, it is understood that any number of sensors measuring any number of physiological signals may be used to assess patient status in accordance with the techniques described herein.

In an embodiment, sensors 16 and 18 are combined within a single sensor capable of detecting a single signal carrying information about both HR and BP. In an embodiment, this sensor may be a pulse oximeter. In this embodiment, sensor unit 12 may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. The light intensity or the amount of light absorbed may then be used to calculate the HR and BP of a patient, among other physiological signals. Techniques for obtaining HR and BP measurements from oximetry data are described in more detail in co-pending, commonly assigned U.S. patent application Ser. No. 12/242,867, filed Sep. 30, 2008, entitled "SYSTEMS AND METHODS FOR NON-INVASIVE CONTINUOUS BLOOD PRESSURE DETERMINATION" and co-pending, commonly assigned U.S. patent application Ser. No. 12/242, 238, filed Sep. 30, 2008, entitled "LASER SELF-MIXING SENSORS FOR BIOLOGICAL SENSING," which are incorporated by reference herein in their entirety.

In an embodiment, sensor unit 12 includes a laser Doppler sensor. Techniques for obtaining information about blood pressure from self-mixed laser Doppler sensors are described in more detail in co-pending, commonly assigned U.S. patent application Ser. No. 12/242,738, filed Sep. 30, 2008, entitled "LASER SELF-MIXING SENSORS FOR BIOLOGICAL SENSING," which is incorporated by reference herein in its entirety.

It will be understood that the present disclosure is applicable to any suitable signals that communicate BP and HR information. It should be understood that the signals may be digital or analog. Moreover, those skilled in the art will recognize that the present disclosure has wide applicability to signals including, but not limited to other biosignals (e.g., electrocardiogram, electroencephalogram, electrogastrogram, phonocardiogram, electromyogram, pathological sounds, ultrasound, or any other suitable biosignal), or any combination thereof. For example, the techniques of the present disclosure could be applied to monitoring the correlation between respiration rate and pathological sounds, or respiration rate and arterial (or venous) pressure fluctuations.

In an embodiment, the sensor unit 12 may be connected to and draw its power from monitor 14 as shown. In another embodiment, the sensor unit 12 may be wirelessly connected to monitor 14 and include its own battery or similar power supply (not shown). In an embodiment, sensor unit 12 may be communicatively coupled to monitor 14 via a cable 24. However, in other embodiments, a wireless transmission device (not shown) or the like may be used instead of or in addition to cable 24.

Monitor 14 may be configured to calculate physiological parameters (e.g., HR and BP) based at least in part on data received from sensor unit 12. In an alternative embodiment, the calculations may be performed on the monitoring device itself and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments to be discussed further below, such as for example, sounding an audible alarm in the event that a patient's physiological parameters are not within a predefined normal range.

In the illustrated embodiment, system 10 may also include a multi-parameter patient monitor 26. The monitor 26 may include a cathode ray tube display, a flat panel display (as shown) such as a liquid crystal display (LCD) or a plasma display, or may be any other type of monitor now known or later developed. Multi-parameter patient monitor 26 may be configured to calculate physiological parameters and to provide a display 28 for information from monitor 14 and from other medical monitoring devices or systems (not shown). In an embodiment to be discussed further below, multi-parameter patient monitor 26 may be configured to display estimates of a patient's BP and HR from monitor 14. Monitor 26 may include a speaker 30.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable physiological signal calibration device. Calibration device 80 may be communicatively coupled to monitor 14 via cable 82, and/or may communicate wirelessly (not shown). For example, calibration device 80 may take the form of any invasive or non-invasive BP monitoring or measuring system used to generate reference BP measurements for use in calibrating BP monitoring techniques. Calibration device 80 may also access reference measurements stored in memory (e.g., RAM, ROM, or a storage device). For example, in some embodiments, calibration device 80 may access reference measurements from a relational database stored within calibration device 80, monitor 14, or multi-parameter patient monitor 26.

Figure 3:
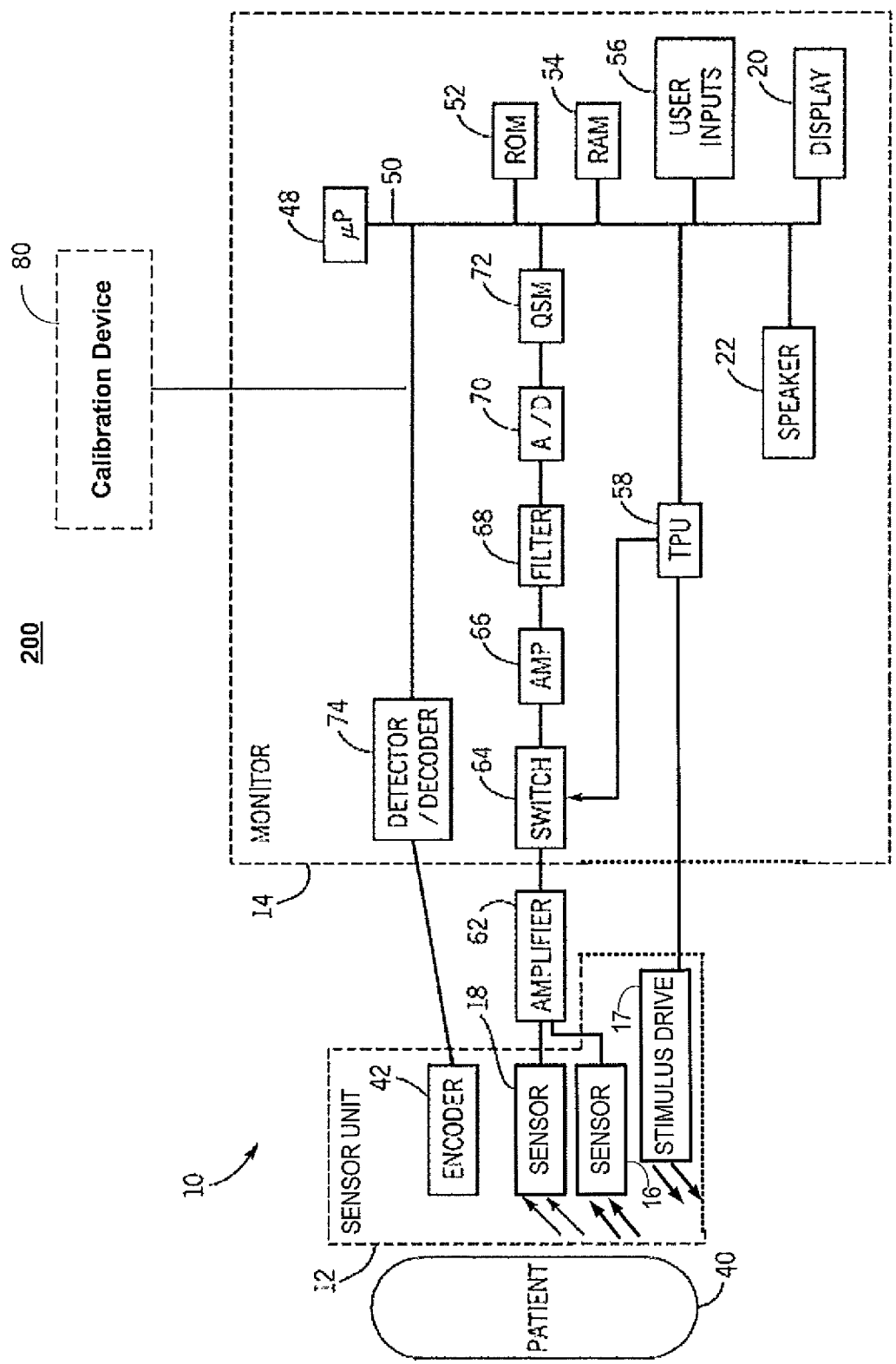
FIG. 3 is a block diagram of the illustrative BP/HR monitoring system of FIG. 2 coupled to a patient in accordance with some embodiments.

FIG. 3 is a block diagram of a BP/HR monitoring system 200, such as system 10 of FIG. 2, which may be coupled to a patient 40 in accordance with an embodiment. Certain illustrative components of sensor unit 12 and monitor 14 are illustrated in FIG. 3.

Sensor unit 12 may include encoder 42. In an embodiment, encoder 42 may contain information about sensor unit 12, such as what type of sensors it includes (e.g., whether the sensor is a pressure transducer or a pulse oximeter). This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which BP and HR are determined based on the signal or signals received at sensor unit 12. For example, some pulse oximetry sensors rely on equations to relate an area under a pulse of a photoplethysmograph (PPG) signal to determine BP. These equations may contain coefficients that depend upon a patient's physiological characteristics as stored in encoder 42. In some embodiments, encoder 42 may include a memory or a coded resistor which stores one or more of the following types of information for communication to monitor 14: the types of sensors included in sensor unit 12; the wavelength or wavelengths of light used by an oximetry sensor when included in sensor unit 12; a signal threshold for each sensor in the sensor array; any other suitable information; or any combination thereof.

In an embodiment, signals from sensor unit 12 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a stimulus drive 17, which may control when a stimulus is used to apply a signal to the patient, the response to which communicates information about BP, HR or other physiological processes. For example, stimulus drive 17 may be an light emitter in an oximetry configuration. Techniques for obtaining BP measurements by inducing perturbations in a patient via a stimulus drive are described in more detail in co-pending, commonly assigned U.S. patent application Ser. No. 12/248,738, filed Oct. 9, 2008, entitled "SYSTEMS AND METHODS USING INDUCED PERTURBATION TO DETERMINE PHYSIOLOGICAL PARAMETERS," which is incorporated by reference herein in its entirety. TPU 58 may also control the gating-in of signals from sensor unit 12 through an amplifier 62 and a switching circuit 64. The received signal or signals from sensor unit 12 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple sensors included in sensor unit 12.

In an embodiment, microprocessor 48 may determine the patient's physiological parameters, such as BP and HR, using various algorithms and/or look-up tables based on the value of the received signals and/or data from sensor unit 12. For example, when sensor unit 12 includes an oximetry sensor, microprocessor 48 may generate an equation that represents empirical data associated with one or more patients that includes various BP measurements associated with different areas under a pulse of a PPG signal. Signals corresponding to information about patient 40 may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The signal from the patient can be degraded by noise, among other sources. One source of noise is electromagnetic coupling from other electronic instruments. Movement of the patient also introduces noise and affects the signal. For example, the contact between the sensor and the skin can be temporarily disrupted when movement causes either to move away from the skin. Another source of noise is ambient light that reaches the light detector in an oximetry system.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals may involve operations that reduce the amount of noise present in the signals or otherwise identify noise components in order to prevent them from affecting measurements of physiological parameters derived from the sensor signals.

BP/HR monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described above, reference measurements from calibration device 80 may be accessed by microprocessor 48 for use in calibrating the sensor measurements and determining physiological signals from the sensor signal and empirical data of one or more patients.

Figure 4:
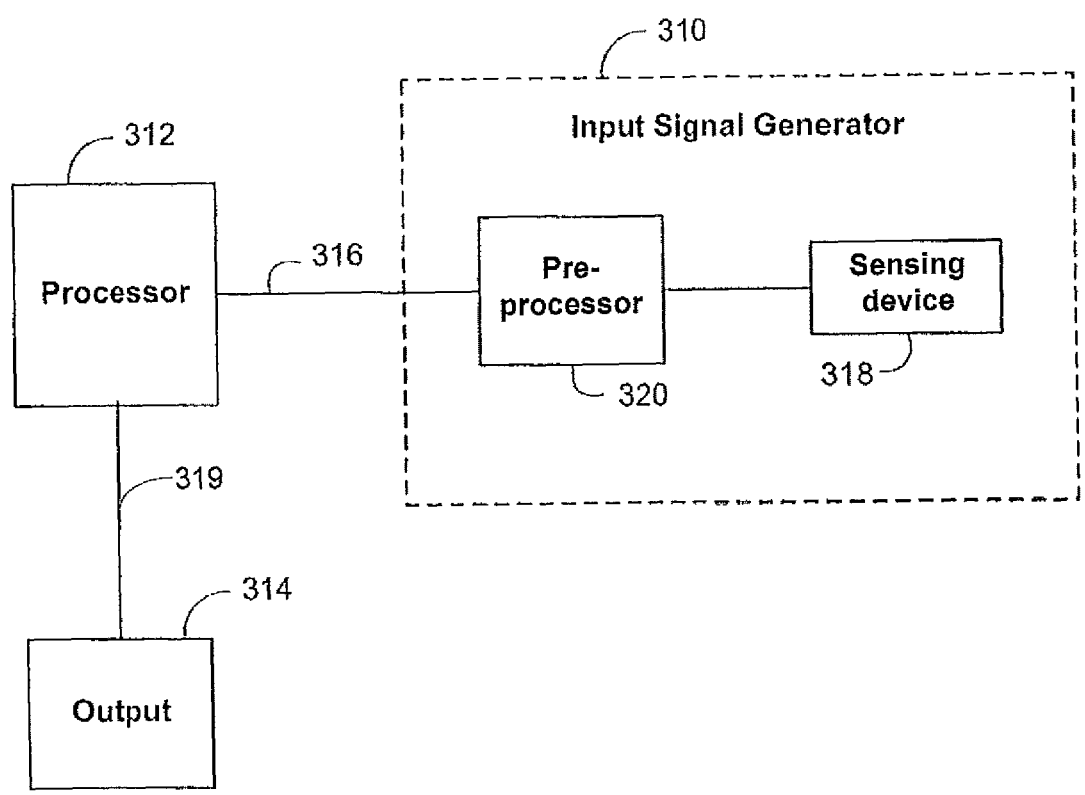
FIG. 4 is a block diagram of an illustrative signal processing system in accordance with some embodiments.

FIG. 4 is an illustrative processing system 300 in accordance with an embodiment. In an embodiment, input signal generator 310 generates an input signal 316. As illustrated, input signal generator 310 includes pre-processor 320 coupled to sensing device 318. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing techniques to the signal generated by sensing device 318. For example, pre-processor 320 may apply a pre-determined transformation to the signal provided by the sensing device 312 to produce an input signal 316 that can be appropriately interpreted by processor 312. Pre-processor 320 may also perform any of the following operations to the signal provided by the sensing device 318: reshaping the signal for transmission; multiplexing the signal; modulating the signal onto carrier signals; compressing the signal; encoding the signal; and filtering the signal.

In the embodiment of FIG. 4, signal 316 is be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, be configured of analog electronic components. Processor 312 may perform some or all of the calculations associated with the BP/HR monitoring methods of the present disclosure. For example, processor 312 may correlate the BP and HR signals and identify a characteristic of the correlation, to be discussed further below. Processor 312 may also perform any suitable signal processing to filter signal 316, such as any suitable band-pass filtering, adaptive filtering, closed-loop filtering, and/or any other suitable filtering, and/or any combination thereof. Processor 312 may also receive input signals from additional sources (not shown). For example, processor 312 may receive an input signal containing information about treatments provided to the patient. These additional input signals may be used by processor 312 in any of the calculations or operations it performs in accordance with the BP/HR monitoring system 300.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In an embodiment, processor 312 may store physiological measurements or previously received data from signal 316 in a memory device for later retrieval. Processor 312 may be coupled to a calibration device (not shown) that may generate or receive as input reference measurements for use in calibrating calculations.

Processor 312 is coupled to output 314 through patient status indicator signal 319, and may be coupled through additional signal pathways not shown. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In an embodiment, patient status indicator signal 319 includes at least one of an identification of a medical condition of the patient; an alert; a current HR measurement; a current BP measurement; a HR/BP correlation measurement; another current physiological measurement; an estimated patient status; and an estimated patient outcome. In some embodiments, patient status indicator signal 319 will be stored in a memory device or recorded in another physical form for future, further analysis.

It will be understood that system 300 may be incorporated into system 10 (FIGS. 2 and 3) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch, other piece of jewelry, or cellular telephone). In such embodiments, a wireless transceiver (not shown) may also be included in system 300 to enable wireless communication with other components of system 10. As such, system 10 may be part of a fully portable and continuous BP/HR monitoring solution.

Figure 5:
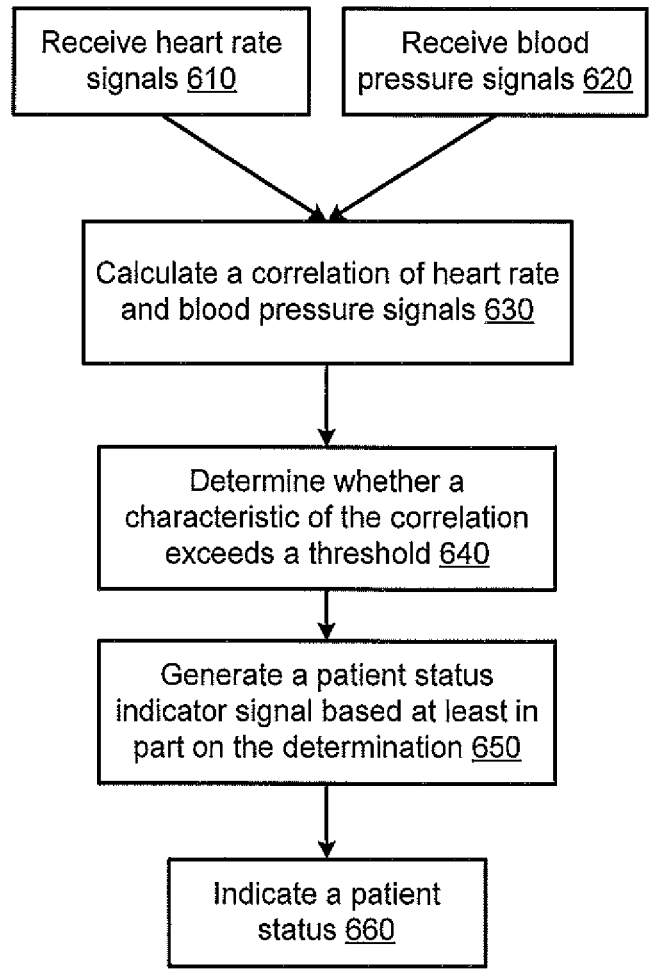
FIG. 5 is a flow diagram of an illustrative BP/HR monitoring process performed in accordance with some embodiments.

FIG. 5 is a flow diagram of an illustrative BP/HR monitoring process performed in accordance with some embodiments. The steps in this process will be discussed with continued reference to the systems and apparatus described in FIGS. 2-4. Processor 312 receives a HR signal (step 610) and receives a BP signal (step 620). These signals are transmitted to processor 312 from input signal generator 310 via input signal 316. As discussed above, these steps 610 and 620 may be accomplished by receiving a single signal at processor 312. For example, signal 316 may be an oximetry signal that contains information about both HR and BP.

In response to receiving the HR and BP signals, processor 312 calculates a correlation of the signals (step 630). The calculated correlation can be any measure of the degree to which the two signals vary together, i.e. the tendency of the two signals to increase simultaneously and decrease simultaneously. In one embodiment, the correlation is calculated in accordance with $$\frac{\Delta HR}{\Delta BP},$$

where $\Delta HR$ measures a change in HR over an interval and $\Delta BP$ measures a change in BP over the same interval. In another embodiment, the correlation is the Pearson product moment correlation, calculated in accordance with $$\frac{1}{T-1}\sum_{i=1}^{T}\left(\frac{HR_i - \overline{HR}}{s_{HR}}\right)\left(\frac{BP_i - \overline{BP}}{s_{BP}}\right),$$

where T is the number of samples or measurements; $HR_i$ and $BP_i$ are the ith HR and BP measurements, respectively; $\overline{HR}$ and $\overline{BP}$ are the sample mean HR and BP, respectively; and $s_{HR}$ and $s_{BP}$ are the sample standard deviations of HR and BP, respectively.

In another embodiment, the correlation between two continuous-time signals x(t) and y(t), each of which have a duration at least T time units is calculated as a cross-correlation function in accordance with $$\frac{1}{T}\int_0^T x(\tau)y(t+\tau)\,d\tau.$$

In another embodiment, the correlation between two discrete-time signals x[n] and y[n] (e.g., those that are sampled by a computer), each of which have a duration at least T samples, is calculated as a cross-correlation function in accordance with $$\frac{1}{T}\sum_{m=0}^{T-1} x[m]y[n+m].$$

Note that such correlation calculations are synonymous with convolution calculations when one of the signals under investigation is symmetric. It will be understood that the foregoing are merely examples of techniques for calculating a correlation in accordance with the methods and systems described herein.

In response to calculating a correlation of the HR and BP signals, processor 312 determines whether a characteristic of the correlation exceeds a threshold (step 640). A characteristic of the correlation may include any feature of the calculated correlation, or recently-calculated correlations, including a maximum, minimum or average value; median or mode values; a derivative or rate of change; a second derivative; an amplitude at a signal landmark; the timing of a signal landmark; a similarity of the correlation over an interval to a pre-defined shape or pattern; a function of the current correlation; a function of the correlation over a time period; and a frequency content of the correlation.

Processor 312 may retrieve a threshold from memory such as ROM 52 or RAM 54 or may retrieve it from a remote storage device. This threshold signifies the point at which the characteristic of the correlation indicates a patient condition warranting an indication, such as a dangerous patient condition. For example, a patient may reach a point at which an increasing heart rate no longer corresponds to an increasing cardiac output due to compromised left ventricular refill (or, for example, when a patient is experiencing massive hemorrhaging). This point may correspond to a threshold on a characteristic of the correlation. In an embodiment, a characteristic of the correlation is the sign of the correlation, i.e. whether it is positive or negative and the threshold of interest is exceeded when the correlation is negative. In another embodiment, a characteristic of the correlation is the rate of change of the correlation and the threshold of interest is exceeded when the rate of change of the correlation exceeds a fixed negative value (indicating a transition toward negative correlation of HR and BP).

In some embodiments, a history of correlations is used to generate a characteristic of the correlation. In one embodiment, a small negative correlation that persists beyond a duration threshold may indicate a dangerous condition. In another embodiment, a correlation that continues to decrease, even slowly, beyond a duration threshold may indicate a dangerous condition.

Once the processor 312 has determined whether a characteristic of the correlation exceeds a threshold, processor 312 generates a patient status indicator signal 319 based at least in part on the results of the determination (step 650). In an embodiment, processor 312 stores a patient status indicator value associated with the patient status indicator signal 319 in a memory device such as ROM 52 or RAM 54, as discussed in more detail below. In an embodiment, the patient status indicator signal 319 includes an alert when the threshold has been exceeded. In some embodiments, the patient status indicator signal 319 includes at least one of an identification of a medical condition of the patient; an alert; a current HR measurement; a current BP measurement; a HR/BP correlation measurement; and another current physiological measurement. In an embodiment to be discussed further below, the patient status indicator signal 319 includes at least one of a patient status and predicted outcome produced by a predictive computational model based on the HR and BP signals. In an embodiment, the processor 312 determines the patient status indicator signal 319 by querying a look-up table to determine an appropriate patient status value given the results of the comparison between the characteristic of the correlation and the threshold. The look-up table may be stored in ROM 52, RAM 54 or another electronic memory device communicably coupled to processor 312. For example, when the correlation is found to be negative, the processor 312 will find the entry in the look-up table that corresponds to a negative correlation and retrieve the associated patient status value. This associated patient status value may be a specific medical condition (e.g., "tachycardia due to blood loss"), an alert as will be discussed further below, or a prompt for the care provider to input additional information via user inputs 56. The look-up table may also be indexed by patient characteristics as described previously, such as age weight, height, diagnosis, medications, and treatments. In an embodiment, the look-up table may be indexed by previously stored patient status indicator values.

In some embodiments, processor 312 may compute more than one correlation of the HR and BP signals to perform a threshold test for more than one patient condition. In some embodiments, processor 312 may compare each of more than one characteristic of the calculated correlations to a corresponding threshold. In some embodiments, processor 312 may combine the results of each of these comparisons using algebraic or logical operations to determine an appropriate patient status indicator signal 319. In some embodiments, different threshold comparisons may take priority over other threshold comparisons. For example, processor 312 may generate a patient status indicator signal 319 corresponding to "normal" when the correlation exceeds a first positive threshold value, but generate a patient status indicator signal 319 corresponding to "atrial fibrillation" when the correlation exceeds the first threshold value and the rate of change of correlation drops below a second threshold value.

In some embodiments, the processor 312 will use additional information about the patient's physiological state or medical treatment to generate the patient status indicator signal 319. For example, processor 312 may compute a patient's blood oxygenation level when input signal 316 includes an oximetry signal and additionally use this information to generate the patient status indicator signal 319. In another embodiment, processor 312 may detect abnormal pulse shapes in a patient's ECG signal and additionally use this information to generate the patient status indicator signal 319. In another embodiment, processor 312 may generate a patient status indicator signal 319 corresponding to "critical tachycardia" when the correlation exceeds a first positive threshold value and the heart rate exceeds a second positive threshold value.

In another embodiment, the correlation may be considered along with respiratory information to diagnose obstructive sleep apnea (OSA) in sleep studies. OSA is often characterized by cyclic changes in BP and HR, combined with cessation in breathing.

In response to receiving the patient status indicator signal 319, output 314 indicates a patient status (step 660). Output 314 may indicate a patient status by any means useful for alerting a patient and a care provider to a patient status. Output 314 may indicate a patient status by performing at least one of the following in response to the particular patient status indicator signal 319: presenting an alert screen on a display; presenting a warning message on a display; producing a tone or sound; changing a color of a display or a light source; producing a vibration; and sending an electronic message. Output 314 may perform any of these actions in a device close to the patient, or at a mobile or remote monitoring device as described previously. In an embodiment, output 314 produces a continuous tone or beeping whose frequency changes in response to changes in the correlation. In an embodiment, output 314 produces a colored or flashing light which changes in response to changes in the correlation.

Figure 6A:
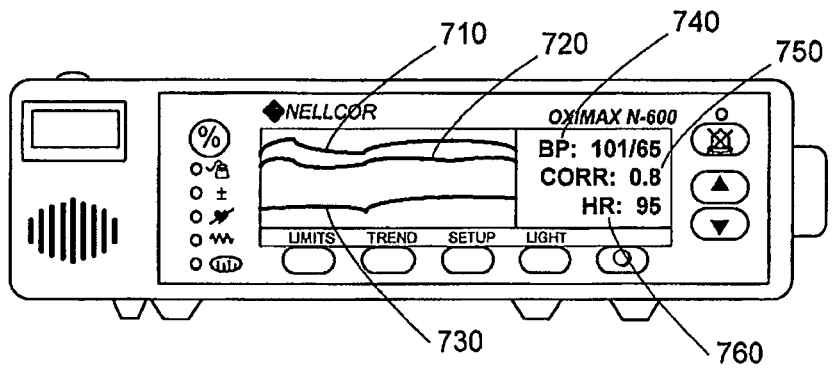
FIGS. 6A-6C depict illustrative BP/HR monitoring system display screens in accordance with some embodiments.
Figure 6B:
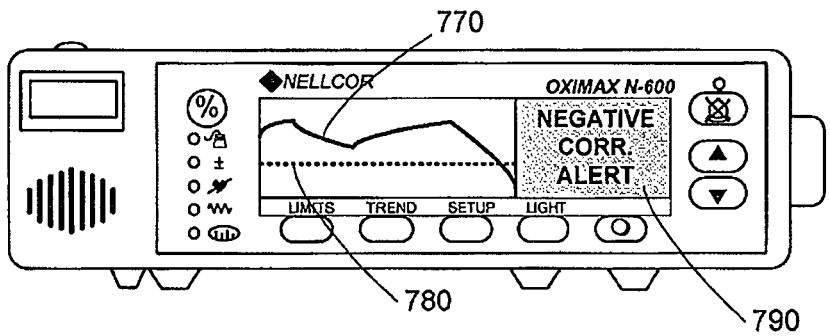
Figure 6C:
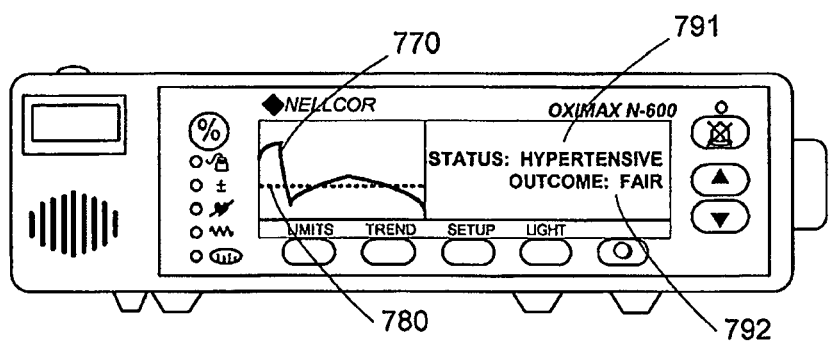

In some embodiments, processor 312 may continuously or periodically perform steps 610-660 and update the patient status indicator signal as the patient's condition changes. In some embodiments, processor 312 performs steps 610-660 at regular intervals. In an embodiment, processor 312 performs steps 610-660 at a prompt from a care provider via user inputs 56. In an embodiment, processor 312 performs steps 610-660 at intervals that change according to patient status. For example, steps 610-660 will be performed more often when a patient is undergoing rapid changes in physiological condition, and will be performed less often as the patient's condition stabilizes FIGS. 6A-6C depict illustrative BP/HR monitoring system display screens in accordance with some embodiments. In FIGS. 6A-6C, display screens are depicted as embedded within a unit similar to monitor 14 of FIG. 2, but it will be understood that these screens are merely illustrative and could be included in the display of any output device 314 as discussed above.

In the embodiment illustrated in FIG. 6A, systolic BP waveform 710, diastolic BP waveform 720 and heart rate waveform 730 are displayed. Additionally, current BP 740, current correlation 750 and current HR 760 are displayed. The waveforms 710-730 and current values 740-760 are communicated to the output 314 by patient status indicator signal 319.

In an embodiment, processor 312 derives the BP and HR waveforms 710-730 from one or more physiological signals. For example, processor 312 may use an oximetry signal, or may use both an electrocardiograph signal and an arterial line signal. In an embodiment, processor 312 calculates improved BP waveforms 710 and 720 by incorporating the HR waveform 730 into the BP calculation. This may be achieved by processor 312 augmenting its calculation of BP waveforms 710 and 720 with the information contained in HR waveform 730 by any one of the following example estimation techniques: a minimum-variance estimator, a maximum-likelihood estimator, a least-squares estimator, a moment estimator, a minimum-mean-square-error estimator, a maximum a posteriori estimator; and an adaptive estimation technique. To perform any of these estimation techniques, processor 312 may use previous measurements of BP, HR and any other physiological signals stored in a memory device. Processor 312 may also use data from other patients as stored in calibration device 80, or statistical parameters stored in ROM 52, RAM 54, encoder 42 or at a remote data storage location. Other estimation techniques may include rule-based systems and adaptive rule-based systems, such as propositional logic, predicate calculus, modal logic, non-monotonic logic and fuzzy logic.

In an embodiment, processor 312 produces confidence intervals for the derived BP waveforms 710-720 using the heart rate waveform 730. Confidence intervals allow a care provider to assess the quality of a particular BP measurement when making decisions about patient care. Processor 312 may use any one of the following example computational techniques to construct confidence intervals for the derived BP waveforms 710-720 using the heart rate waveform 730: sample statistic techniques, likelihood theory, estimating equations and significance testing. When constructing the confidence intervals, processor 312 may retrieve a priori statistical parameters from a memory device such as ROM 52, RAM 54, encoder 42 or at a remote data storage location. Confidence measures may include probability density estimates calculated, for example, using non-parametric Bayesian estimation methods, neural networks, or any suitable heteroassociative function estimation method.

In the embodiment illustrated in FIG. 6B, the display includes a correlation waveform 770 over an interval of time. The level at which the correlation is zero is indicated by dashed line 780. The display of FIG. 6B also includes a warning message 790 alerting the care provider that the correlation waveform 770 has dropped below a previously-calculated or previously-defined threshold, signifying a dangerous medical condition. As discussed previously with respect to FIG. 5, the warning message 790 of FIG. 6B is displayed by output 314 in response to patient status indicator signal 319, and is associated at least in part with the comparison performed by processor 312 in step 640.

FIG. 6C depicts an embodiment in which the correlation waveform 770 is displayed along with estimates of a patient status 791 and a patient outcome 792. These estimates 791 and 792 are determined by processor 312 based on a predictive computational model. In some embodiments, the predictive computational model determines only one of the patient status estimate 791 and the patient outcome estimate 792. In some embodiments, the predictive computational model determines additional estimates of a patient's current physiological status and prognosis. The predictive computational model used by processor 312 may be based in part on at least one of the following data sources: BP waveforms 710 and 720; HR waveform 730; additional physiological signals; patient characteristics; historical data of the patient or other patients; and computational or statistical models of physiological processes. Processor 312 may retrieve any of these data sources from memory such as ROM 52 or RAM 54, from calibration device 80, from an external memory device, or from a remote memory device. The structure of the predictive computational model used by processor 312 may, for example, be based on any of the following models: a neural network, a Bayesian classifier, and a clustering algorithm. In an embodiment, processor 312 develops a predictive neural network based at least in part on historical data from the given patient and other patients. In some embodiments, processor 312 implements the predictive computational model as a hypothesis test. Processor 312 may continually refine or augment the predictive computational model as new patient data is received via input signal 316. Processor 312 may also refine the predictive model based on feedback from the patient or care provider received through the user inputs 56. Other predictive frameworks may include rule-based systems and adaptive rule-based systems such as propositional logic, predicate calculus, modal logic, non-monotonic logic and fuzzy logic.

FIG. 6C depicts a "hypertensive" patient status 791. The patient status estimate 791 may be selected from any number of potential values, and is embedded in the patient status indicator signal 319. The processor 312 determines the appropriate patient status estimate 791 by applying the predictive computational model to the input signal 316. For example, the processor 312 may use a predictive computational model which is capable of producing patient statuses including "normal," "undergoing exertion," "hypotensive," "hypertensive," "blood loss," "tachycardia," "tachyarrhythmia," "bradycardia," "cardiac output reduction" and other statuses.

FIG. 6C also depicts a "fair" patient outcome estimate 792. The patient outcome estimate 792 may be an output of the predictive computational model. Possible patient outcome estimates 792 may include "good," "fair," "poor," "critical" and any other prognostic indication for use in triaging patients or informing care providers of the severity of patient illness.

Figure 7:
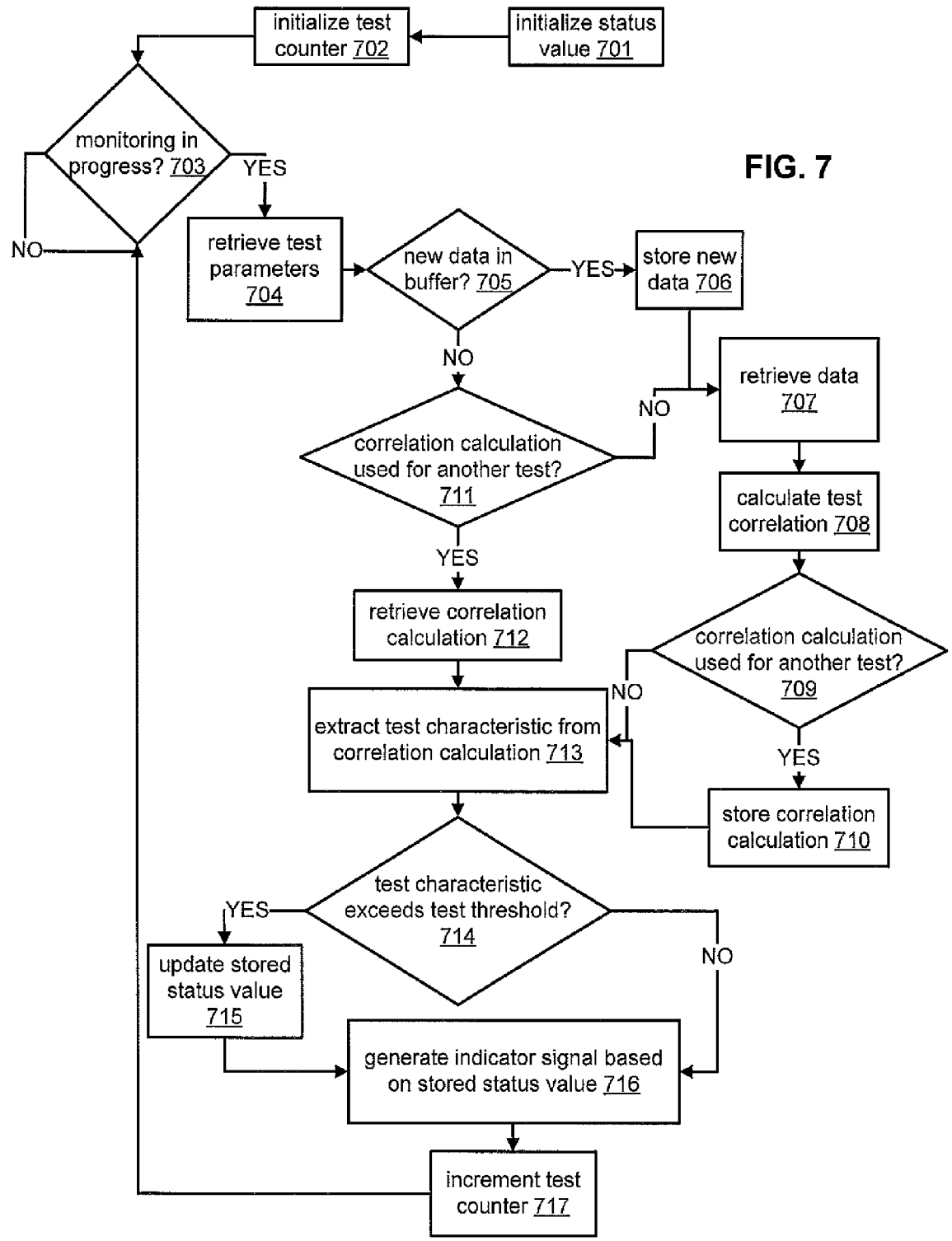
FIG. 7 is a flow diagram of an illustrative BP/HR monitoring process performed in accordance with an embodiment.

FIG. 7 is a flow diagram of an illustrative BP/HR monitoring system in accordance with an embodiment. For purposes of illustration, the process of FIG. 7 will be described as being performed by microprocessor 48 of FIG. 3, but may be performed more generally by processor 312. Upon power-up of the BP/HR monitoring system, microprocessor 48 stores an initial status value (step 701) and an initial test counter value (step 702). These values may be stored in RAM 54, to which the microprocessor 48 is communicably coupled via internal bus 50. The initial status value represents a nominal patient condition, and may be, for example, the value "0" representing a normal patient status. The initial test counter value represents which medical condition microprocessor 48 is currently testing for when comparing a characteristic of the correlation to a threshold (which will be referred to as the "current medical condition"). Microprocessor 48 may be configured to test for more than one medical condition, and each medical condition may be associated with an identifying number. For example, the medical condition "tachycardia" may be associated with identifying number "1" and the medical condition "atrial fibrillation" may be associated with identifying number "2". When the test counter value is equal to the identifying number of a medical condition, microprocessor 48 performs the threshold test associated with that medical condition, as will be discussed in more detail below. Microprocessor 48 will sequentially carry out the performance of the test associated with each medical condition and increment the test counter value at the conclusion of each test.

At step 703, microprocessor 48 determines whether patient monitoring is currently in progress. Microprocessor 48 may make this determination by monitoring the signal produced by sensor unit 12 for a "patient present" condition. For example, when a patient is not being monitored by sensor unit 12, the signal produced by sensor unit 12 may be a near-zero or ambient voltage level, from which microprocessor 48 may conclude that monitoring is not in progress. If microprocessor 48 determines that monitoring is in progress, microprocessor 48 retrieves a set of test parameters corresponding to the current test counter value (step 704). These test parameters may include instructions for carrying out the correlation calculation, instructions for identifying the correlation characteristic and the particular threshold value associated with the medical condition test corresponding to the current medical condition. Microprocessor 48 may retrieve these test parameters from ROM 52 and store the parameters as the current set of test parameters in RAM 54.

Microprocessor 48 determines whether any new input data has been received (step 705) by querying QSM 72 via internal bus 50. If buffer QSM 72 is empty, microprocessor 48 determines whether any other medical condition requires the same correlation calculation as the current medical condition (step 711). Microprocessor 48 may perform this step, for example, by comparing the instructions for the correlation calculation associated with the current medical condition to the instructions for the correlation calculation associated with each of the other medical conditions as stored in ROM 52. If microprocessor 48 determines that another medical condition requires the same correlation calculation as the current medical condition, this correlation calculation is retrieved from RAM 54 (step 712).

Returning to step 705, if new data has been buffered into QSM 72, microprocessor 48 stores this new data in RAM 54 (step 706) and may clear the data stored in QSM 72. Microprocessor 48 then retrieves all of the data necessary to perform the correlation calculation from RAM 54 in accordance with the instructions in the test parameters associated with the current medical condition (step 707). At step 708, microprocessor 48 performs this correlation calculation. Next, microprocessor 48 performs the same comparison as step 711, determining whether any other medical condition requires the same correlation calculation as the current medical condition. If another medical condition requires the same correlation calculation, the calculation performed at step 708 is stored in RAM 54 (step 710). Performing these kinds of checks eliminates redundancy in data storage in RAM 54 and decreases the time required for microprocessor 48 to perform a full cycle of threshold tests for all medical conditions.

At step 713, microprocessor 48 extracts the correlation characteristic from the correlation calculation. The correlation characteristic for the current medical condition is included in the current test parameters associated with the current medical condition, as retrieved by microprocessor 48 from ROM 52. For example, the correlation characteristic may be a rate of change of the calculated correlation, or may be any other characteristic as discussed above. At step 714, microprocessor 48 may determine whether the correlation characteristic exceeds a threshold. As described above, the threshold is also included in the test parameters associated with the current medical condition and was retrieved by microprocessor 48 from ROM 52 in step 704.

If the correlation characteristic exceeds the threshold, microprocessor 48 updates the stored status value in RAM 54 to a new status value associated with the current condition (step 715). For example, if the current medical condition is "tachycardia" and the associated correlation characteristic exceeds the associated threshold, the status value will be updated to "1," where "1" is the status value corresponding to the presence of "tachycardia." If the correlation characteristic does not exceed the threshold at step 714, the stored status value does not change.

At step 716, a patient status indicator signal is generated based upon the stored status value. The patient status indicator signal may include an indication of the stored status value, and may include additional information as described in detail above. Microprocessor 48 increments the test counter at step 717, at which point microprocessor 48 returns to step 703. When there are a finite number of medical conditions stored in ROM 52, microprocessor 48 will perform step 717 by resetting the test counter to its initial value once it performed steps 704-716 for all of the stored conditions, and repeat the full cycle of threshold tests.

The foregoing is merely illustrative of the principles of this disclosure and various modifications can be made by those skilled in the art without departing from the scope and spirit of the disclosure. The following numbered paragraphs may also describe various aspects of the disclosure.

What is claimed is:

1. A method for monitoring patient status with a processor, the method comprising:
    receiving an electronic signal indicative of a patient's heart rate;
    receiving an electronic signal indicative of a patient's blood pressure;
    calculating a correlation of the electronic signal indicative of a patient's heart rate and the electronic signal indicative of a patient's blood pressure;
    determining whether the correlation is positive or negative;
    comparing a characteristic of the correlation to a threshold in response to determining that the correlation is positive;
    generating a patient status indicator signal based on the comparison; and
    indicating, with an output device, a patient status based on the generated patient status indicator signal.

2. The method of claim 1, wherein the characteristic of the correlation comprises a change in heart rate relative to a change in blood pressure.

3. The method of claim 1, wherein the characteristic of the correlation comprises a rate of change in heart rate relative to a rate of change in blood pressure.

4. The method of claim 1, wherein indicating the patient status comprises at least one of displaying the correlation characteristic on a screen, displaying a message associated with the patient status indicator signal, displaying a color associated with the patient status indicator signal, displaying a graphic associated with the patient status indicator signal, and producing a sound associated with the patient status indicator signal.

5. The method of claim 1, further comprising calculating a current blood pressure based at least in part on the received electronic signal indicative of the patient's heart rate.

6. The method of claim 1, further comprising predicting at least one of a patient outcome and current status using a computational model based at least in part on the electronic signal indicative of a patient's heart rate and the electronic signal indicative of a patient's blood pressure.

7. The method of claim 1, wherein the characteristic of the correlation is selected from the group consisting of a maximum value, a minimum value, an average value, a median value, a mode value, a rate of change, a second derivative, an amplitude of a signal landmark, a timing of a signal landmark, a similarity of the correlation over an interval to a pre-defined pattern, a function of the one or more correlations, a frequency content, and any combination thereof.

8. The method of claim 1, further comprising:
    calculating more than one correlation of the electronic signal indicative of the patient's heart rate and the electronic signal indicative of the patient's blood pressure;
    comparing each of more than one characteristic of the more than one correlation to a respective corresponding threshold;
    generating the patient status indicator signal based on the comparisons; and
    combining the comparisons using at least one of algebraic operations and logical operations, wherein generating the patient status indicator signal is further based on the combined comparisons.

9. A system for monitoring patient status with a processor, the system comprising:
    a processor capable of receiving at least one input signal, the processor configured to:
        receive an electronic signal indicative of a patient's heart rate;
        receive an electronic signal indicative of a patient's blood pressure;
        calculate a correlation of the electronic signal indicative of a patient's heart rate and the electronic signal indicative of a patient's blood pressure;
        determine whether the correlation is positive or negative;
        compare a characteristic of the correlation to a threshold in response to determining that the correlation is positive;
        generate a patient status indicator signal based on the comparison; and
    an output device communicably coupled to the processor configured to indicate a patient status based on the generated patient status indicator signal.

10. The system of claim 9, wherein the characteristic of the correlation comprises a change in heart rate relative to a change in blood pressure.

11. The system of claim 9, wherein the characteristic of the correlation comprises a rate of change in heart rate relative to a rate of change in blood pressure.

12. The system of claim 9, wherein the output device is further configured to perform at least one of displaying the correlation characteristic on a screen, displaying a message associated with the patient status indicator signal, displaying a color associated with the patient status indicator signal, displaying a graphic associated with the patient status indicator signal, and producing a sound associated with the patient status indicator signal.

13. The system of claim 9, wherein the processor is further configured to calculate a current blood pressure based at least in part on the received electronic signal indicative of the patient's heart rate.

14. The system of claim 9, wherein the processor is further configured to predict at least one of a patient outcome and current status using a computational model based at least in part on the electronic signal indicative of a patient's heart rate and the electronic signal indicative of a patient's blood pressure.

15. The system of claim 9, wherein the characteristic of the correlation is selected from the group consisting of a maximum value, a minimum value, an average value, a median value, a mode value, a rate of change, a second derivative, an amplitude of a signal landmark, a timing of a signal landmark, a similarity of the correlation over an interval to a pre-defined pattern, a function of the one or more correlations, a frequency content, and any combination thereof.

16. The system of claim 9, wherein the processor is further configured to:
- calculate more than one correlation of the electronic signal indicative of the patient's heart rate and the electronic signal indicative of the patient's blood pressure;
- compare each of more than one characteristic of the more than one correlation to a respective corresponding threshold;
- generate the patient status indicator signal based on the comparisons; and
- combine the comparisons using at least one of algebraic operations and logical operations; and
- generate the patient status indicator signal based on the combined comparisons.

17. A system for monitoring patient status, the system comprising:
- non-transitory computer readable medium storing computer executable instructions for:
  - receiving an electronic signal indicative of a patient's heart rate;
  - receiving an electronic signal indicative of a patient's blood pressure;
  - calculating a correlation of the electronic signal indicative of a patient's heart rate and the electronic signal indicative of a patient's blood pressure;
  - determining whether the correlation is positive or negative;
  - comparing a characteristic of the correlation to a threshold in response to determining that the correlation is positive; and
  - generating a patient status indicator signal based on the comparison; and
- an output device configured to indicate a patient status based on the generated patient status indicator signal.

18. The system of claim 17, wherein the characteristic of the correlation comprises a change in heart rate relative to a change in blood pressure.

19. The system of claim 17, wherein the characteristic of the correlation comprises a rate of change in heart rate relative to a rate of change in blood pressure.

* * * * *